United States Patent [19]

Paik et al.

[11] Patent Number: 4,652,440

[45] Date of Patent: Mar. 24, 1987

[54] METHOD OF STABLY RADIOLABELING ANTIBODIES WITH TECHNETIUM AND RHENIUM

[76] Inventors: Chang H. Paik, 7631 Trail Run Rd., Falls Church, Va. 22042; Richard C. Reba, 11405 Toulone Dr., Potomac, Md. 20854; William C. Eckelman, 2 Harvard Ct., Rockville, Md. 20850

[21] Appl. No.: 606,731

[22] Filed: May 3, 1984

[51] Int. Cl.$^4$ .................. A61K 43/00; A61K 49/00
[52] U.S. Cl. ........................................ 424/1.1; 424/9
[58] Field of Search ..................... 424/1.1, 9; 534/14

[56] References Cited

U.S. PATENT DOCUMENTS

| | | | |
|---|---|---|---|
| 4,331,647 | 5/1982 | Goldenberg | 424/1.1 |
| 4,421,735 | 12/1983 | Haber et al. | 424/1.1 |
| 4,478,815 | 10/1984 | Burchiel et al. | 424/1.1 |

OTHER PUBLICATIONS

Steigman et al, Int. J. Appl. Rad. Isotopes, 26 (1975) 601–609.
Khaw et al, J. Nucl. Med, 23 (1982) 1011–1019.
Hnatowich et al, Int. J. Appl. Rad. Isotopes, 33 (1982) 327–332.
Hnatowich et al, J. Immunol. Meth., 65 (1983) 147–157.

*Primary Examiner*—Christine M. Nucker
*Attorney, Agent, or Firm*—Bernard D. Saxe

[57] ABSTRACT $^{99m}$Tc-labeling of antibodies and antibody fragments, either unconjugated or conjugated to DTPA, is effected in the presence of molar excess of free or carrier-bound DTPA to substantially completely inhibit direct technetium binding to non-stable binding sites on the antibody. The resultant $^{99m}$Tc-labeled antibody has a stable label and is useful for, inter alia, tumor imaging by gamma scintigraphy and/or tumor therapy. Rhenium-labeling can be similarly effected.

18 Claims, No Drawings

METHOD OF STABLY RADIOLABELING ANTIBODIES WITH TECHNETIUM AND RHENIUM

BACKGROUND OF THE INVENTION

The present invention relates to an improved method for labeling antibodies and/or antibody fragments with radionuclides of technetium or rhenium to obtain stable labeling.

Antibodies and/or antibody fragments which are labeled with radionuclides have been shown to be useful for radioimmunoassays, radioimmunodetection of tumors and tumor therapy. In the latter, tumor-related applications as disclosed, e.g., in patents to Goldenberg, U.S. Pat. Nos. 4,331,647, 4,348,376, 4,361,544 and 4,444,744, one of the preferred radionuclides used for antibody labeling was I-131, because of its convenient half life and the relative ease with which it can be introduced into immunoglobulin molecules and/or fragments thereof. Radioisotopes of iodine have been available for a long time, but have the disadvantage that only a few radioisotopes have appropriate half lives and energies for external imaging, especially imaging using gamma scintigraphic devices. Another disadvantage of using radioiodine for antibody labeling is the in vivo instability of the label, a significant amount of the radioisotope being excreted as elemental iodine within a relatively short time after injection of a radioiodinated antibody into the bloodstream.

Other radioisotopes which are readily available, and which also have convenient half lives and emission energies for gamma imaging, include indium-111 ($^{111}$In) and technetium-99m ($^{99m}$Tc). In order to bind $^{111}$In to immunoglobulin molecules or fragments, it is necessary to conjugate a metal chelating agent to the protein since $^{111}$In itself does not bind to immunoglobulin protein. Hnatowich et al, *J. Imm. Methods*, 65, 147-157 (1983), disclose a method for binding $^{111}$In to antibodies by conjugating diethylenetriaminepentaacetic acid (DTPA) to antibodies, followed by incubation of the DTPA-conjugated antibody with $^{111}$In salts.

Technetium can be bound directly to antibody protein, e.g., as disclosed by Pettit et al, *J. Nucl. Med.*, 21, 59-62 (1980); and Crockford et al, U.S. Pat. No. 4,323,546, or indirectly using DTPA-conjugated antibody, as disclosed in, e.g., Khaw et al, *J. Nucl. Med.*, 23, 1011-1019 (1982). However, several problems are associated with both direct and indirect $^{99m}$Tc-labeling of immunoglobulin protein. On the one hand, antibodies which are directly labeled with $^{99m}$Tc have been reported to be unstable in vivo, i.e., a significant proportion of the radionuclide dissociates from the labeled antibody fairly quickly upon injection of the labeled antibody into the bloodstream. When labeled antibody is used for external imaging, this instability leads to accumulation of radioactivity in locations other than those at which the radiolabeled antibody localizes. This reduces the resolution of the method by attenuating the localized radioactivity and by increasing the background activity due to non-specific distribution of the radioisotope. Rhodes et al, *Tumor Imaging*, chapter 12, pages 111-124 (Masson Publ., USA, 1982), disclose that unstable antibodies directly labeled with $^{99m}$Tc could be purified using an elaborate permeation chromatographic method. Khaw et al, supra, disclose some loss in antibody activity upon labeling DTPA-conjugated anticardiac myosin Fab fragments with $^{99m}$Tc, as well as significant liver activity in a scintigram taken 12 hours after injection of the labeled antibody into dogs in which were induced experimental myocardial infarctions. The liver activity was tentatively attributed to incomplete clearance of colloids. No specific determination was made of the percentage of stable label.

Other difficulties reported by earlier workers for $^{99m}$Tc labeling of antibodies are reoxidation of reduced technetium ($Tc^{+3}$ and/or $Tc^{+4}$) to pertechnetate ($TcO_4^-$) and hydrolysis of reduced technetium ions to form radiocolloids. Residual pertechnetate is difficult to remove as are the colloids, and both tend to contribute to undesirable non-specific background radiation.

OBJECTS OF THE INVENTION

One object of the present invention is to provide a method for direct and/or indirect labeling of antibodies and/or antibody fragments with radionuclides of technetium or rhenium to produce stable labeling without the need for elaborate purification procedures.

Another object of the invention is to provide a kit suitable for generating $^{99m}$Tc-labeled antibodies and/or antibody fragments in a simple, one-step procedure capable of producing an injectable solution of stable labeled antibodies without the need for chromatographic purification.

Upon further study of the specification and appended claims, further objects and advantages of this invention will become apparent to those skilled in the art.

SUMMARY OF THE INVENTION

These objects are attained by providing a method for labeling antibodies or antibody fragments with radionuclides of technetium or rhenium to obtain stable labeling, comprising the steps of reacting a reduced radioisotope of technetium or rhenium with an antibody or antibody fragment, or a diethylenetriaminepentaacetic acid-conjugated antibody or antibody fragment, in the presence of free or carrier-bound diethylenetriaminepentaacetic acid (DTPA), the amount of DTPA being sufficient to substantially completely inhibit binding of said reduced technetium or rhenium to non-stable binding sites of said antibody or antibody fragment, or said DTPA-conjugated antibody or antibody fragment; and recovering the resultant stably labeled antibody or antibody fragment, or DTPA-conjugated antibody or antibody fragment.

The method of the invention is used to produce antibodies and/or antibody fragments directly or indirectly labeled with technetium or rhenium radionuclides.

A kit suitable for preparation of an injectable solution of the foregoing labeled antibodies is also provided.

DETAILED DISCUSSION

The present inventors have carried out extensive and systematic labeling experiments which have revealed that immunoglobulin protein, e.g., whole IgG or fragments such as F(ab')$_2$, Fab' or Fab, contains both stable and non-stable labeling sites for reduced technetium or rhenium ions. The "non-stable site" (which may be one or more sites) has a high capacity but a low affinity for reduced technetium (it will be understood hereinafter that reduced rhenium ions are included when the more commonly used technetium ions are discussed, since the chemistry of technetium and rhenium is substantially the same for labeling purposes, although binding constants may be somewhat different). This non-stable site accounts for 85% of the total direct labeling of F(ab')₂ fragments and 76% of the total labeling of IgG with reduced $^{99m}$Tc. The second site gives rise to a stable label and accounts for 15% and 24% of the total labeling of F(ab')₂ and IgG with $^{99m}$Tc, respectively.

Surprisingly and unexpectedly, it has been found that direct labeling of antibodies in the presence of diethylenetriaminepentaacetic acid (DTPA), in a sufficient molar excess, can substantially completely inhibit labeling of the non-stable site, so that substantially only a stable labeled antibody is produced. In this discussion, the term "antibody" will be understood to represent intact immunoglobulin, especially IgG, immunoglobulin fragments such as those mentioned hereinabove, and intact immunoglobulin and/or fragments to which are conjugated (covalently bound) one or more molecules of DTPA. Labeling of DTPA-conjugated antibodies permits a higher percentage of incorporation of stable technetium radioisotope. Labeling in the further presence of DTPA also prevents formation of unstable label, and permits production of a high radiochemical yield of stably labeled DTPA-conjugated antibody.

It appears that DTPA acts as a competitive ligand which binds reduced technetium more tightly than the non-stable binding site of the antibody, but less tightly than the stable binding site thereof. Accordingly, labeling in the presence of free DTPA produces technetium-labeled antibody and DTPA-complexed technetium, wherein the antibody binds technetium ions only at the high-affinity, stable binding site.

A further unexpected and surprising advantage of the present method is that it substantially avoids the formation of colloid during the course of the labeling process. In addition, appropriate proportions of reducing agent and exclusion of oxygen will prevent the accumulation of residual pertechnetate as a contaminant.

The efficiency of the labeling reaction is influenced by the molar ratio of DTPA to antibody, the amount of stannous ions, the pH of the medium, the buffer system, the atmosphere and the incubation time of stannous ion with DTPA and antibody. The effect of these parameters can be appreciated by conducting controlled experiments wherein they are varied one at a time. A convenient antibody for such studies is the F(ab')₂ fragment of commercially available rabbit antibody against human serum albumin (HSA). This antibody (hereinafter designated F(ab')₂) is divalent for antigen binding and has a physiological half life which is compatible with $^{99m}$Tc labeling. It will be appreciated that this example is merely illustrative and that other intact immunoglobulin and other fragments will behave similarly, although there will be some variation in the specific parameters.

A first study was carried out using F(ab')₂ produced from the rabbit anti-HSA antibody by the procedure of Parham, *J. Immunol.*, 131, 2895–2902 (1983).

The study was carried out in 0.1M acetate buffer to maintain the pH at 4.5. Reaction solutions were purged with nitrogen and the reaction vials were maintained at a negative pressure in order to minimize the formation of residual pertechnetate. The ratio of DTPA to F(ab')₂ and the ratio of DTPA to stannous ion were varied in order to optimize the complexation of $^{99m}$Tc with DTPA in the presence of F(ab')₂. As control experiments, free DTPA and F(ab')₂ at a DTPA: F(ab')₂ molar ratio of 4 were incubated with stannous chloride at a DTPA:Sn²⁺ molar ratio of 0.33, 1.0, 2.0 and 4.0 for 30 minutes at pH 4.5. These solutions were than incubated with 200 uCi of $^{99m}$TcO₄⁻ for 15 minutes. The final concentration of F(ab')₂ was $3.1 \times 10^{-5}$M (155 ug/50 ul). The complexation reactions at the above DTPA/Sn²⁺ ratios gave rise to about equal percentages of both DTPA—$^{99m}$Tc and F(ab')₂-$^{99m}$Tc. However, the formation of DTPA-$^{99m}$Tc was proportional to the DTPA/F(ab')₂ ratio up to a ratio of 8 and leveled off at 84% DTPA-$^{99m}$Tc. This indicates that a fraction of total F(ab')₂-$^{99m}$Tc has a higher formation constant than that of DTPA-$^{99m}$Tc. This represents direct labeling of the stable site of the antibody fragment with $^{99m}$Tc. Side reactions producing $^{99m}$TcO₄⁻ and $^{99m}$Tc-colloid were negligible under these conditions. The results are shown in Table I.

TABLE I $^{99m}$Tc complexation of DTPA in competition with F(ab')₂ ($3.1 \times 10^{-5}$ M) in 0.1 M acetate at pH 4.5.

| DTPA F(ab')₂ | DTPA Sn²⁺ | SnCl₂ 2H₂O ug/ml | DTPA-$^{99m}$Tc (%) | F(ab')₂-$^{99m}$Tc (%) | $^{99m}$Tc colloids (%) |
|---|---|---|---|---|---|
| 1 | 0.33 | 21.0 | 19.2(14.2–24.7) | 80.8(75.3–85.8) | — |
| 2 | 0.33 | 42.0 | 28.9(26.2–32.1) | 71.1(67.9–72.8) | — |
| 4 | 0.17 | 168.0 | 23.6(23.3–23.9) | 54.1(51.7–56.4) | 22.3(19.7–25.0) |
| 4 | 0.33 | 84.0 | 52.9(51.9–53.9) | 47.1(46.1–48.1) | — |
| 4 | 1.0 | 28.0 | 49.1(43.1–55.1) | 50.9(44.9–56.9) | — |
| 4 | 2.0 | 14.0 | 59.4(53.3–65.5) | 40.6(34.5–46.7) | — |
| 4 | 4.0 | 7.0 | 51.7(47.8–53.2) | 48.3(46.0–52.2) | — |
| 8 | 2.0 | 28.0 | 82.2(75.0–93.0) | 17.8( 7.0–25.0) | — |
| 12 | 1.5 | 56.0 | 81.0(72.0–90.0) | 19.0(10.0–28.0) | — |
| 16 | 2.0 | 56 | 84.5(80.0–89.0) | 15.5(11.0–20.0) | — |
| 20 | 2.5 | 56.0 | 84.5(83.8–85.2) | 15.5(14.8–16.2) | — |
| 28 | 3.5 | 56.0 | 87.6(87.4–88.1) | 12.4(11.9–12.6) | — |

The data are averages of duplicate to quadrupulet experiments and their ranges in parenthesis.

The relative reactivity between F(ab')₂-conjugated DTPA and free DTPA toward $^{99m}$Tc was investigated by reacting reduced $^{99m}$Tc with a solution containing 4 DTPA molecules conjugated per F(ab')₂ and various molar ratios of free DTPA to F(ab')₂-conjugated-DTPA. Competition studies at molar ratios of 1, 2, 4, and 6.5 produced radiochemical yields of F(ab')₂-DTPA-$^{99m}$Tc of 33.0, 28.6, 14.2 and 9.0%, the data having been obtained after subtraction of 16% from the total $^{99m}$Tc incorporated into F(ab')₂ fragments to eliminate the radioactivity incorporated by direct binding to the stable site of the antibody. Using these data, the average relative rate of formation of F(ab')₂-DTPA-$^{99m}$Tc to free DTPA-$^{99m}$Tc was calculated to be 0.82. The data show that addition of an excess of free DTPA effectively inhibits binding of $^{99m}$Tc to the unstable sites of the F(ab')₂. The data also show that a molar ratio of total DTPA (i.e., free DTPA plus conjugated DTPA)

to F(ab')$_2$ of about 8:1 will substantially completely inhibit binding of $^{99m}$Tc to the unstable binding site of the F(ab')$_2$ antibody fragment. Using F(ab')$_2$ to which are conjugated 4 DTPA molecules, in the further presence of 4 molar equivalents of free DTPA, it is possible to obtain up to about 55% radiochemical yield of stably labeled F(ab')$_2$-DTPA-$^{99m}$Tc, using the method of the invention. It is emphasized that $^{99m}$Tc is bound to both the stable site on the antibody and to the DTPA ligands. The results of the competitive experiments are summarized in Table II.

TABLE II

| Competition between F(ab')$_2$-DTPA and DTPA for $^{99m}$Tc | | | | |
|---|---|---|---|---|
| Conjugated DTPA | Free DTPA | F(ab')$_2$-DTPA-$^{99m}$Tc[a] | DTPA-$^{99m}$Tc | Relative[b] |
| F(ab')$_2$ | F(ab')$_2$ | % | % | Rate |
| 4.0 | 4.0 | 33.0(27.5,32.5,39.0) | 51.0(45.0,51.5,56.5) | 0.64 |
| 4.0 | 8.0 | 28.6(26.0,31.3) | 55.4(52.7,58.0) | 1.03 |
| 4.0 | 16.0 | 14.2(12.3,16.2) | 69.8(67.8,71.7) | 0.81 |
| 4.0 | 26.0 | 9.0(8.1,9.9) | 75.0(74.1,75.9) | 0.78 |
| | | | Average | 0.82 |

[a]The data are obtained after subtracting 16% from the total $^{99m}$Tc incorporated into F(ab')$_2$ fragments.
[b]The formation rate of F(ab')$_2$-DTPA-$^{99m}$Tc relative to DTPA-$^{99m}$Tc and calculated based on the following formula.

$$\text{Relative Rate} = \frac{\% \text{ F(ab')}_2\text{-DTPA-}^{99m}\text{Tc}}{\% \text{ DTPA-}^{99m}\text{Tc}} \times \frac{\text{DTPA}}{\text{conjugated DTPA}}$$

A pH of 4-6 is optimal for the stannous ion reduction of pertechnetate and the labeling reaction. Below a pH of about 4, some deactivation of the antibody occurs due to the high acidity. Above a pH of about 6, some stannous hydroxide begins to form and this leads to production of Tc-colloid. Buffering is advantageously effected with acetate. Citrate and ascorbate are less satisfactory, since at buffering concentrations, these ions compete for reduced technetium ions and interfere with labeling. It can also be seen from the data that an excess of stannous ion over pertechnetate, normally several thousand-fold, should be used to prevent loss of reduced technetium due to reoxidation by, e.g., adventitious oxygen. This side reaction can also be further minimized by carrying out the reaction in an inert atmosphere, e.g., under nitrogen, argon and the like, and/or in vacuo, i.e., by withdrawing the gas above the reaction solution, e.g., using a syringe.

In addition to the preferred stannous salts, e.g., the readily available stannous chloride, or stannous tartrate, and the like, other reducing agents can be used to reduce pertechnetate to $Tc^{3+}/Tc^{4+}$ for antibody labeling, e.g., dithionite, ferrous ascorbate, sodium borohydride and the like, as disclosed in e.g., Deutsch et al., "Technetium Chemistry and Radiopharmaceuticals", Prog. Inorg. Chem., 30, pgs. 84ff (1983), and refs. therein.

It is seen from the data of Table I that a sharp reduction in labeling of the non-stable site of the antibody occurs between a DTPA/F(ab')$_2$ ratio of 4 and 8, the latter ratio insuring substantially complete inhibition of direct labeling at the non-stable site. However, even a ratio of 6 will result in nearly complete inhibition of unstable label. Ratios higher than 8 are acceptable, but a large excess of DTPA is unnecessary and wasteful.

When intact IgG is labeled with reduced technetium, it is advantageous to use a DTPA/IgG ratio of at least about 14:1 to substantially inhibit binding of the technetium to the non-stable site. It will be appreciated that other fragments and other species of antibodies will have somewhat different characteristics with respect to the binding constants of the stable and nonstable technetium binding sites, relative to the binding constant of DTPA. However, the simple parametric variations illustrated in Tables I and II will quickly establish the optimum ratio for substantially complete inhibition of unstable direct binding, evident from the rise in formation of DTPA-$^{99m}$Tc and decrease in antibody-99mTc with an increase in DTPA/antibody ratio, up to a plateau when the non-stable binding is substantially completely inhibited. A similar behavior is seen for rhenium labeling.

It has been found that a delicate balance exists between the advantages and disadvantages of using DTPA-conjugated antibody as opposed to directly labeling an antibody. On the one hand, the attachment of DTPA molecules to the antibody is almost invariably accompanied by at least some loss of antibody immunoreactivity. On the other hand, conjugation of DTPA to the antibody permits a higher degree of stable labeling, when the labeling is carried out according to the method of the invention. Moreover, DTPA-conjugated antibody clears faster than unconjugated antibody, which is advantageous in reducing background radiation for gamma scintigraphic imaging. The extent of loss of antibody immunoreactivity which accompanies DTPA conjugation can be determined by well-known procedures, e.g., that disclosed by Paik et al, supra. For certain antibodies specific to tumor-associated antigens, the benefits of conjugating DTPA to the antibody may be outweighed by a significant loss of immunoreactivity. However, this will depend on the characteristics of the antibody and upon how much DTPA is conjugated. In each individual case, an appropriate balance must be struck.

The biodistribution in percent dose per gram of F(ab')$_2$-DTPA-$^{99m}$Tc, F(ab')$_2$-$^{99m}$Tc and F(ab')$_2$-DTPA$^{111}$In were determined. This study was carried out by first incubating a mixture of free DTPA and F(ab')$_2$ ($3.1 \times 10^{-5}$M, 155 ug), at a DTPA/F(ab')$_2$ ratio of 6, with stannous ion at a DTPA/$Sn^{2+}$ molar ratio of 1, in 0.1M acetate buffer at pH 4.5 for 1 hour. This solution was incubated with $^{99m}$Tc. The same conditions were used for radiolabeling F(ab')$_2$-DTPA containing 2 DTPA molecules per F(ab')$_2$, in the presence of 4 molar equivalents of free DTPA. As a control, the same amounts of stannous ion and $^{99m}$Tc were used to directly label F(ab')$_2$, in the absence of DTPA. As a further control, the F(ab')$_2$-DTPA was labeled with $^{111}$In analogously to the labeling of the intact anti-HSA IgG in Paik et al, supra. Affinity-purified F(ab')$_2$D-TPA-$^{99m}$Tc and F(ab')$_2$-$^{99m}$Tc (specific activities of 1-2 uCi per ug) containing 2-4 uCi were each separately injected into the tail vein of mice in order to study their relative distributions in comparison to affinity-purified F(ab')$_2$-DTPA-$^{111}$In. The biodistributions in % dose per gram are shown in Table III.

It can be seen that tissue accumulation of radioisotope from F(ab')$_2$-DTPA-$^{99m}$Tc and F(ab')$_2$-DTPA-$^{111}$In was quite similar, within experimental error. On the other hand, tissue accumulation of $^{99m}$Tc from directly labeled F(ab')$_2$ was much lower, which is interpreted as further supporting the non-stability of the majority of the $^{99m}$Tc labeling of the antibody in the absence of molar excess DTPA. The data also support the rationale for the present invention in that use of molar excess DTPA for labeling F(ab')$_2$-DTPA produces stable $^{99m}$Tc-labeled antibody fragments which behave similarly to $^{111}$In-labeled fragments insofar as their tissue distribution is concerned. It is known that $^{111}$In-labeled antibodies and/or antibody fragments specific against tumor-associated antigens can be used for external gamma scintigraphic imaging. Similarly, such antibodies which are stably labeled with $^{99m}$Tc are attractive reagents for gamma scintigraphy.

TABLE III

Biodistribution in % dose per gram of F(ab')$_2$-DTPA-$^{99m}$Tc, F(ab')$_2$-$^{99m}$Tc, and F(ab')$_2$-DTPA-$^{111}$In in mice at 2.5 hr post injection.

| Organ | F(ab')$_2$-DTPA-$^{99m}$Tc$^a$ | F(ab')$_2$-$^{99m}$Tc$^b$ | F(ab')$_2$-DTPA-$^{111}$In$^c$ | |
|---|---|---|---|---|
| Lung | 2.45 ± 0.88 | 0.76 ± 0.12 | 6.27 | (5.73~6.81) |
| Liver | 3.28 ± 1.22 | 1.06 ± 0.06 | 3.66 | (3.49~3.84) |
| Spleen | 2.24 ± 1.11 | 0.49 ± 0.04 | 2.66 | (2.48~2.84) |
| Kidney | 9.10 ± 2.27 | 5.90 ± 0.97 | 9.34 | (8.74~9.93) |
| Bone | 1.05 ± 0.29 | 0.35 ± 0.02 | 1.42 | (1.42~1.43) |
| Muscle | 0.85 ± 0.20 | 0.32 ± 0.09 | 0.81 | (0.57~1.05) |
| Blood | 9.62 ± 2.37 | 2.91 ± 0.56 | 19.67 | (17.90~21.44) |

$^{a,b}$The data are average numbers of quintuplicate experiments and their standard deviation.
$^c$The data are average numbers of duplicate experiments, with ranges in parenthesis.
F(ab')$_2$-DTPA was prepared using the cyclic DTPA dianhydride method.

The divalent F(ab')$_2$ fragment clears faster than IgG. This property, combined with the advantageous half life of a $^{99m}$Tc label and the optimum gamma emission of $^{99m}$Tc, makes F(ab')$_2$-$^{99m}$Tc antibody fragments against tumor-associated antigens particularly attractive where one object is to avoid the use of subtraction agents or technqiues.

It is advantageous to be able to carry out the method of the invention in a simple, one-step process for preparing a solution of $^{99m}$Tc-labeled antibody which is ready for injection into patients for gamma imaging. A simple kit can be prepared for this purpose which is ready to use in most clinical settings having minimal nucler medicine capabilities. The kit comprises a sterile lyophilizate prepared by lyophilizing a solution containing a source of stannous ions, e.g., SnCl$_2$, or other convenient stannous salts, the chosen antibody or antibody fragment, either unconjugated or conjugated to DTPA to an extent which does not significantly destroy the immunoreactivity of the antibody, and free or carrier-bound DTPA, in an amount such that the ratio of total DTPA to antibody is sufficient to substantially inhibit binding to non-stable antibody binding sites. Advantageously, the solution is buffered at a pH of about 4-6, a higher pH being preferable because the lyophilized antibody has a longer shelf life at a pH which is closer to neutrality. The solution is lyophilized under sterile conditions, either in an appropriate vial for later labeling or under conditions wherein it can be transferred to an appropriate vial, e.g., a mini-vial, and the vial is sealed under negative pressure, all of the foregoing operations being preferably effected under sterile conditions.

In order to prepare a solution of $^{99m}$Tc-labeled antibody for injection, it will be sufficient to prepare a sterile solution of $^{99m}$TcO$_4^-$ in neutral saline, the solution being injected into the vial and incubated, with agitation. The pH of the reconstituted labeling solution is about that of the buffered solution prior to lyophilization. After appropriate incubation, e.g., for 10 minutes-1 hour preferably about 15 minutes, the solution is filtered and the filtrate is recovered for injection.

It is convenient to use DTPA conjugated to a carrier, e.g., sepharose beads or the like, in place of free DTPA. The behavior of the carrier-bound DTPA as a competitive ligand to substantially completely inhibit the binding of reduced technetium ions to non-stable binding sites on the antibody is substantially equivalent to the behavior of free DTPA, although the binding constants will not be identical. Sepharose-conjugated DTPA can be readily prepared by reacting amine-derivatized Sepharose beads, e.g., AH-Sepharose-4B (Pharmacia Fine Chemicals, Piscataway, N.J.), a bead-formed agarose gel treated with cyanogen bromide, and then 1, 6-diaminohexane, with DTPA cyclic dianhydride, using conditions substantially analogous to those of Paik et al., supra.

Other carriers are possible, having amine groups or other functional groups convertible thereto, and being compatible with the labeling medium and reagents, but the commercially available amine-derivatized polysaccharides are preferred.

The use of carrier-bound DTPA permits recovery of an injectable solution of labeled antibody merely by withdrawing the incubated labeling solution through a filter, e.g., a 0.20u millipore filter, which is available commercially with fittings such that it can be inserted between the needle and barrel of a syringe. The filtered solution in the syringe barrel can then be injected through another needle directly into the patient.

Thus, a $^{99m}$Tc-labeling kit according to the invention may be used by any licensed medical facility, using a commercially available pertechnetate generator, e.g., the technetium-99m generator sold by New England Nuclear, Boston, MA.

In the event that it is desired to avoid the use of carrier-bound DTPA, the $^{99m}$Tc-DTPA complex can be removed by chromatography, e.g., on a Sephadex G-50 column.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of Anti-human Serum Albumin F(ab')$_2$

Rabbit antibody to human serum albumin (HSA), is cleaved and the F(ab')$_2$ fragment thereof is recovered, using the procedure of Parham.

A 100 mg sample of rabbit anti-HSA antibody (Boehringer Mannheim Biochemicals, Indianapolis, IN.) and 2 mg of pepsin (Sigma Chemical Co., St. Louis, Mo.), in 10 ml of 0.1M NaOAc, is incubated at 37° C. for 12 hours. The Fc fragment precipitate is centrifuged, and the supernatant solution decanted. Acetate buffer is exchanged for phosphate buffered saline (PBS) by Minicon membrane filtration (Amicon, Danvers, MA) and the resultant solution is introduced on a Sephadex G-150 column and eluted with PBS. The F(ab')$_2$ fraction elutes after the IgG fraction, as a fairly homogeneous fraction, which is rechromatographed on a protein-A affinity column to remove traces of IgG. A yield of about 25-30 mg of purified F(ab')$_2$ is obtained. The resultant F(ab')$_2$ fragment is affinity purified using an affinity column containing sepharose-4B-conjugated HSA, using the procedure of Paik et al., *J. Nucl. Med.*, 24, 1158-1163 (1983) for the corresponding IgG in the foregoing reference. The F(ab')$_2$ is conjugated with either 2 or 4 molar equivalents of DTPA, using the cyclic dianhydride method of Paik et al., supra. Reduction of immunoreactivity is inversely proportional to the number of DTPA molecules conjugated to the antibody fragment.

EXAMPLE 2

Preparation of Labeled F(ab')$_2$ (A) A nitrogen-purged solution of 300 ug of the F(ab')$_2$ prepared in Example 1 ($3.1 \times 10^{-5}$M), free DTPA ($6.2 \times 10^{-4}$M), and SnCl2.2H20 ($2.5 \times 10^{-4}$M) in 0.1M acetate buffer at pH 4.5 is incubated for 30 minutes at room temperature. To the incubated solution is added 20 uCi of pertechnetate in saline, from a commercial generator (New England Nuclear, Boston, MA.), and the solution is incubated for 15 minutes at R.T. The reaction is conveniently effected in a mini-vial sealed with a rubber septum, purged with nitrogen and evacuated by withdrawal of the gaseous atmosphere above the surface of the solution by pulling on the syringe plunger until a strong vacuum is produced and withdrawing the syringe, the septum preserving the partial vacuum in the mini-vial.

The labeled F(ab')$_2$ is isolated by mixing with 1 ml of BSA and chromatographing on Sephadex G-50 to separate $^{99m}$Tc-F(ab')$_2$ from $^{99m}$Tc-DTPA.

(B) The DTPA-conjugated F(ab')$_2$ having 2 equivalents of DTPA conjugated to the F(ab')$_2$, produced in Example 1, the solution also containing free DTPA in an amount such that the ratio of total DTPA to F(ab')$_2$ is 8:1, is incubated with stannous chloride and labeled with $^{99m}$Tc by a procedure analogous to Example 2(A), and the F(ab')$_2$-DTPA-$^{99}$mTc is recovered and purified apalogously to the preceding example.

(C) AH-Sepharose 4B (Pharmacia) is treated with DTPA cyclic dianhydride, using the conditions of Paik et al, supra, to produce DTPA-sepharose beads, containing $10^{-6}$-$10^{-4}$ millimoles DTPA per milligram of DTPA-sepharosebeads. The procedures of parts (A) and (B) of this example are repeated, except that free DTPA is replaced by an amount of the foregoing DTPA-sepharose beads sufficient to provide about one molar equivalent of bound DTPA per equivalent of free DTPA used in the preceding parts. After incubation, the solution containing the labeled antibody is withdrawn from the reaction vial through a syringe equipped with a 0.20u millipore filter assembly interposed between the syringe needle and the syringe barrel (Millipore Corp., Bedford, MA.). The filtered solution in the syringe is ready for injection.

(D) Part (C) of this example is repeated, except that, prior to addition of the solution of $^{99m}$TcO$_4$-, the buffered solution of antibody, DTPA-sepharose-and stannous chloride, the buffering being effected at pH 6, is lyophilized under sterile conditions. The solution is reconstituted under sterile conditions by injection of an appropriate volume of $^{99m}$TcO$_4$- solution, and the remainder of the procedure is effected as in part (C). Again, a filtered, sterile solution of $^{99m}$Tc-labeled F(ab')$_2$-DTPA or F(ab')$_2$ is produced in the syringe, ready for injection into a patient or animal.

(E) A lyophilized reagent solution, as prepared in part (D) of this example, prior to incubation with pertechnetate, is stored for six months at 5° C. Reconstitution of the solution by injection with pertechnetate solution according to part (D) results in substantially the same degree and quality of labeling, showing that the lyophilized solution is substantially stable to relatively long periods of storage in the refrigerator.

The preceding examples can be repeated with similar success by substituting the generically or specifically described reactants and/or operating conditions of this invention for those used in the, preceding examples. In particular, whole IgG, Fab, etc. can be used in place of F(ab')$_2$; $^{186}$ReO$_4$- can be used instead of $^{99m}$TcO$_4$-; polyvinyl alcohol beads can be used instead of sepharose; stannous tartrate can be used instead of stannous chloride, or another reducing agent such as dithionite can be used to reduce TcO$_4$-. The foregoing are merely illustrative, and other equivalent embodiments are possible and contemplated.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for labeling antibodies or antibody fragments with radionuclides of technetium or rhenium to obtain stable labeling, comprising the steps of reacting a reduced radioisotope of technetium or rhenium with an antibody or antibody fragment, or a diethylenetriaminepentaacetic acid conjugated antibody or antibody fragment, in the presence of free or carrier-bound diethylenetriaminepentaacetic acid (DTPA), the amount of DTPA being sufficient to substantially completely inhibit binding of said reduced technetium or rhenium to non-stable binding sites of said antibody or antibody fragment, or said DTPA-conjugated antibody or antibody fragment; and recovering the resultant stably labeled antibody or antibody fragment, or DTPA-conjugated antibody or antibody fragment.

2. The method of claim 1, wherein said radioisotope is $^{99m}$Tc.

3. The method of claim 2, wherein an antibody fragment is labeled, said antibody fragment being an F(ab')$_2$ fragment.

4. The method of claim 3, wherein said amount of DTPA is such that the molar ratio of DTPA to F(ab')$_2$ is at least about 8:1.

5. The method of claim 2, wherein a DTPA-conjugated antibody fragment is labeled, said DTPA-conjugated fragment being a DTPA-conjugated F(ab')$_2$ fragment.

6. The method of claim 5, wherein said amount of DTPA is such that the molar ratio of DTPA and conjugated DTPA to F(ab')$_2$ is at least about 8:1.

7. The method of claim 6, wherein about 2-4 moles of DTPA are conjugated to said F(ab')$_2$ fragment, and about 4-6 moles of non-antibody-computed DTPA are also present in said reaction per mole of said F(ab')$_2$ fragment.

8. A composition suitable for use in preparing an antibody or antibody fragment having a stable label of a radionuclide of technetium or rhenium, comprising:
   (a) an antibody or antibody fragment, or a DTPA-conjugated antibody or antibody fragment;
   (b) free or carrier-bound DTPA, in a molar ratio to said antibody or antibody fragment sufficient to substantially completely inhibit binding of said radionuclide to non-stable binding sites of said antibody or antibody fragment; and
   (c) a reducing agent for pertechnetate or perrhenate.

9. The composition of claim 8, wherein said reducing agent is a stannous ion-containing compound.

10. The composition of claim 8, wherein said DTPA is carrier-bound DTPA.

11. The composition of claim 10, wherein said carrier-bound DTPA is DTPA covalently bound to sepharose beads.

12. A lyophilized composition which is produced by lyophilizing a solution of the composition of claim 10, buffered at a pH of 4-6.

13. A method of producing an antibody or antibody fragment stably labeled with $^{99m}$Tc, comprising the step of reacting the lyophilized composition of claim 12 with a solution of $^{99m}$TcO$_4$; whereby a solution of $^{99m}$Tc-labeled antibody or antibody fragment is obtained.

14. The method of claim 13, which further comprises the step of filtering the solution of $^{99m}$Tc-labeled antibody or antibody fragment and recovering a solution of $^{99m}$Tc-labeled antibody free of the carrier-bound DTPA.

15. The method of claim 14, wherein said filtration is effected by use of a syringe equipped with removable filter means, whereby an injectable solution of antibody or antibody fragment stably labeled with $^{99m}$Tc is directly obtained in said syringe.

16. A kit for labeling antibodies, comprising the lyophilized composition of claim 12, and a container for said composition adapted to receive a solution of pertechnetate or perrhenate.

17. The method of claim 2, wherein whole immunoglobulin is labeled, and wherein the molar ratio of DTPA to immunoglobulin is at least about 14:1.

18. The composition of claim 8, wherein the molar ratio of DTPA to antibody is at least about 8:1.

* * * * *